United States Patent [19]

Müller et al.

[11] Patent Number: 5,324,836

[45] Date of Patent: Jun. 28, 1994

[54] PROCESS FOR THE PREPARATION OF (6S)- AND (6R)-TETRAHYDROFOLIC ACID

[75] Inventors: Hans R. Müller, Schaffhausen; Martin Ulmann, Dachsen; Josef Conti, Schaffhausen, all of Switzerland; Günter Mürdel, Tengen-Büsslingen, Fed. Rep. of Germany

[73] Assignee: Eprova Akteingesellschaft, Schaffhausen, Switzerland

[21] Appl. No.: 44,886

[22] Filed: Apr. 8, 1993

Related U.S. Application Data

[63] Continuation of Ser. No. 821,151, Jan. 16, 1992, abandoned.

[30] Foreign Application Priority Data

Jan. 16, 1991 [CH] Switzerland .................. 00108/91-1

[51] Int. Cl.$^5$ .................................. C07D 475/04
[52] U.S. Cl. .................................................. 544/258
[58] Field of Search .................... 544/258; 514/249

[56] References Cited

U.S. PATENT DOCUMENTS

| | | | |
|---|---|---|---|
| 3,468,886 | 9/1969 | Mosher et al. | 544/258 |
| 4,665,176 | 5/1987 | Hirai et al. | 544/258 |
| 4,959,472 | 9/1990 | Wood et al. | 544/258 |
| 5,006,655 | 4/1991 | Müller et al. | 544/258 |
| 5,010,194 | 4/1991 | Müller et al. | 544/258 |
| 5,134,235 | 7/1992 | Müller et al. | 544/258 |
| 5,173,488 | 12/1992 | Haeger | 514/249 |

FOREIGN PATENT DOCUMENTS

| | | | |
|---|---|---|---|
| 0356934 | 3/1970 | European Pat. Off. | |
| 0266042 | 5/1988 | European Pat. Off. | 544/258 |
| 0348641 | 1/1990 | European Pat. Off. | |
| 2063027 | 7/1971 | Fed. Rep. of Germany | 544/259 |
| 3821875 | 2/1990 | Fed. Rep. of Germany | |
| 48-32120 | 10/1973 | Japan | 544/258 |

OTHER PUBLICATIONS

Abstract of JP 73-0312120 (Eisai) 1973.

Temple, Jr. et al., "Preparation and Purification of L-(+)-5-Formyl-5, 6,7,8-tetrahydrofolic Acid," *Journal of Medicinal Chemistry*, vol. 22, No. 6, Jun. 1979, pp. 731-734.

Rees et al., "Asymmetric Reduction of Dihydrofolate Using Dihydrofolate Reductase and Chiral Boron-Containing Compounds," *Tetrahedron*, vol. 41, No. 1, 1986, pp. 117-136.

Feeney et al., "Hydrogen-1 Nuclear Magnetic Resonance Study of the Complexes of Two Diastereoisomers of Folinic Acid with Dihydrofolate Reductase," *Biochemistry*, vol. 20, No. 7, 1981, pp. 1837-1842.

Kwee et al., "Asymmetric Reduction of L-Folic Acid at Chiral Electrodes," *Bioelectrochemistry and Bioenergetics*, vol. 7, 1980, pp. 693-698, *J. Electroanal. Chem.*, vol. 116, 1980, pp. 693-698.

Boyle et al., "Asymmetric Hydrogenation of a Carbon-Nitrogen Double Bond in Folic Acid," *J. Chem. Soc. Chem. Comm.*, vol. 10, 1974, pp. 375-376.

Frick et al., *Helv. Chim. Acta*, 57, 2658-2661 (1974).

*Primary Examiner*—Donald G. Daus
*Attorney, Agent, or Firm*—Millen, White, Zelano & Branigan

[57] ABSTRACT

For the preparation of (6S)- and (6R)-tetrahydrofolic acid and their addition salts with a sulfonic acid or with sulfuric acid, (6R,S)-tetrahydrofolic acid is reacted with a sulfonic acid or with sulfuric acid, the resulting acid addition salt is fractionally crystallized and, if desired, the (6S)- or (6R)-tetrahydrofolic acid is liberated from the resulting diastereomeric acid addition salts by treatment with a base and isolated.

14 Claims, No Drawings

PROCESS FOR THE PREPARATION OF (6S)- AND (6R)-TETRAHYDROFOLIC ACID

This application is a continuation-in-part of U.S. application Ser. No. 07/821,151, filed Jan. 16, 1992, now abandoned.

BACKGROUND OF THE INVENTION

This invention relates to a process for the preparation of N-[4-[[(2-amino-1,4,5,6,7,8,-hexahydro-4-oxo-(6S)-pteridinyl)methyl]amino]benzoyl]-L-glutamic acid (hereinafter called (6S)-tetrahydrofolic acid) and its salts and N-[4-[[(2-amino-1,4,5,6,7,8-hexahydro-4-oxo-(6R)-pteridinyl)methyl]amino]benzoyl]-L-glutamic acid(hereinafter called (6R)-tetrahydrofolic acid) and its salts.

Tetrahydrofolic acid derivatives contain 2 asymmetric centers. In this case, owing to the synthesis of these derivatives from folic acid, N-(pteroyl)-L-glutamic acid, the optically active C atom contained in the glutamic acid residue is present in the L-form, whereas the optically active C atom in position 6 formed by hydrogenation of the double bond in the 5,6-position of the pteroyl radical is in the racemic, (6R,S)-form. Synthetic derivatives of tetrahydrofolic acid therefore consist of a 1:1 mixture of 2 diastereomers. On natural occurrence, for example in the liver, the tetrahydrofolates are found only in one diastereomeric form, 5,6,7,8-tetrahydrofolic acid being in the (6S)-form.

As medicaments, tetrahydrofolates are mainly used as the calcium salt of 5-formyl-5,6,7,8-tetrahydrofolic acid (leucovorin) or 5-methyl-5,6,7,8-tetrahydrofolic acid for the treatment of megaloblastic folic acid anemia, as an antidote for increasing the tolerability of folic acid antagonists, especially of aminopterin and methotrexate in cancer therapy ("leucovorin rescue"), for increasing the therapeutic effect of 5-fluorouracil and for the treatment of autoimmune diseases such as psoriasis and rheumatoid arthritis and for increasing the tolerability of certain antiparasitics, for example trimethoprim-sulfamethoxazole, in chemotherapy. Tetrahydrofolic acid is used as the basic substance for the preparation of diverse tetrahydrofolic acid derivatives.

Efforts to prepare (6S)- or (6R)-tetrahydrofolic acid have been based on:
enzymatic methods
physicochemical methods
chemical methods Enzymatic methods comprise reduction, normally carried out chemically, of folic acid to 7,8-dihydrofolic acid and subsequent enzymatic reduction thereof to (6S)-5,6,7,8-tetrahydrofolic acid, for example according to L. Rees et. al., Tetrahedron 42(1), 117–36 (1986) or EP-A2-0,356,934. However, these processes can only be stopped with difficulty in the chemical step at the 7,8-dihydrofolic acid stage and also typically give only very small space-time yields in the enzymatic step, require expensive co-factors such as NADPH and necessitate an usually complex working-up methodology. Methods for the enzymatic preparation of optically pure tetrahydrofolic acid known hitherto are not suitable for the preparation of this compound on the industrial scale.

The separation of the diastereomer pairs was also attempted by means of chromatography, J. Feeney et. al., Biochemistry, 20, 1837, (1981). These methods are not suitable for the preparation of the diastereomers on the industrial scale.

An asymmetric reduction of folic acid on chiral electrodes is also known from the group of physicochemical processes, S. Kwee et. al., Bioelectrochem. Bioenerg. 7, 693–698, (1980). Owing to the concentrations of folic acid (typically $10^{-3}$M) permitted during the reduction and the removal of the asymmetric inductor, which can only be carried out with difficulty, after reduction has taken place, these reactions, however, cannot be employed for industrial preparation.

From the field of chemical synthesis, the possibility of asymmetric hydrogenation of folic acid in the presence of an optically active catalyst exists, for example according to P. H. Boyle, et. al., J. Chem. Soc. Chem. Commun. (1974), 10, 375–6. However, this requires the use of very expensive catalysts, which, after homogeneous catalysis has taken place, can only be separated off with great loss of the product.

There is to date therefore still no industrially utilizable process for obtaining optically pure tetrahydrofolic acid.

SUMMARY OF THE INVENTION

An object of this invention is to provide a simple, industrially utilizable and economical method for the preparation of tetrahydrofolic acid.

Upon further study of the specification and appended claims, further objects and advantages of this invention will become apparent to those skilled in the art.

It has now surprisingly been found that correspondingly optically enriched tetrahydrofolic acid addition salt is precipitated from aqueous solutions of (6R,S)-tetrahydrofolic acid or its salts after addition of sulfonic acids or sulfuric acid. This can be removed by filtration. The diastereomeric addition salt can be isolated from the filtrate. Both salts can then be purified both chemically and optically by recrystallization and/or liberation of tetrahydrofolic acid and subsequent conversion to the salt. It is all the more surprising that optical resolution takes place during the crystallization of the sulfonic acid or sulfuric acid addition salt as no optical enrichment can be detected by preparation/recrystallization of other salts, for example the hydrochloric acid addition salt (W. Frick, et. al., Helv. Chim. Acta, 57, 2658–61 (1974)). No enrichment of one of the epimeric forms of tetrahydrofolic acid can be achieved even with other strong acids such as hydrobromic acid, hydriodic acid, nitric acid, phosphoric acid, formic acid, oxalic acid, chloro-, dichloro- and trichloroacetic acid.

The invention relates to a process for the preparation of (6S)- and (6R)-tetrahydrofolic acid and of their addition salts with sulfonic acids or with sulfuric acid, characterized in that (6R,S)-tetrahydrofolic acid is reacted with a sulfonic acid or with sulfuric acid, resulting acid addition salt is fractionally crystallized and, if desired, the (6S)- and/or (6ER)-tetrahydrofolic acid is liberated from the resulting diastereomeric acid addition salts by treatment with a base and isolated.

The (6R,S)-tetrahydrofolic acid used here can be employed either as the isolated product or alternatively preferably directly in situ as the product of reduction of folic acid.

Sulfonic acids suitable for the process according to the invention include aromatic sulfonic acids having 6–14 C atoms, araliphatic sulfonic acids having 7–9 C atoms or aliphatic sulfonic acids having 1–3 C atoms. Examples of suitable romantic sulfonic acids include but are not limited to benzenesulfonic acid, toluenesulfonic acids, xylenesulfonic acids, nitrobenzenesulfonic acids, chlorobenzenesulfonic acids nitrootoluenesulfonic acids, naphthalenesulfonic acids, substituted naphthalenesulfonic acids, wherein the substituents include, for example, alkyl of 1-3 C atoms, hydroxy and/or nitro, naphthalenedisulfonic acids, camphorsulfonic acids, benzimidazolesulfonic acids, wherein the substituents include, for example, aryl, alkyl of 1-3 C atoms and/or hydroxy, substituted benzimidazolesulfonic acids, species thereof being, for example, 2-phenylbenzimidazole-5-sulfonic acid, among others.

A suitable araliphatic sulfonic acid is, for example, phenylmethanesulfonic acid, and suitable aliphatic sulfonic acids include, for example, methanesulfnic acid and ethanesulfonic acids.

Preferred addition salts for the process according to the invention are the benzenesulfonic acid, toluenesulfonic acid, and sulfuric acid addition salts.

The crystallization is carried out from a polar medium. A suitable medium is in particular water or a mixture of water and lower aliphatic water-soluble carboxylic acids, preferably acetic acid or lactic acid; or liquid water-soluble amides such as, for example, formamide, dimethylformamide, dimethylacetamide, 1-methylpyrrolidone and 2-piperidinone. The mixture generally contains at least about 50% water. The use of such a mixture normally increases the optical purity of the products, but the yield may decrease. Depending on the desired purity and the particular starting material, the optimum reaction conditions can be determined without difficulty by routine experimentation. For example, the times and temperatures depend on various factors such as the use or non-use of seeding, the tendency of a given acid addition salt to crystallize in a given solvent, as well as the concentration of the product in the solvent. Generally, an excess of sulfonic or sulfuric acid with respect to the (6S)-content is recommended for favorable yields. For the same reason, at least equivalent amounts of total added acids against total (6R,S)-content should be used.

Owing to the sensitivity of tetrahydrofolic acid to oxidation, it is preferred to use an oxidation inhibitor such as, for example, 2-mercaptoethanol.

During the crystallization the acid addition salt of (6S)-tetrahydrofolic acid as a rule precipitates first - the diastereomeric (6R)-compound is enriched in the filtrates. The optically enriched tetrahydrofolic acid can be very easily liberated again from the salts obtained by addition of a base.

A further possibility of chemical and optical purification is offered by the recrystallization of (6S)-or (6R)-tetrahydrofolic acid acid addition salts and/or the conversion to a salt with a sulfonic acid and/or sulfuric acid carried out subsequently to the liberation of the tetrahydrofolic acid.

As a result of this process, (6S)- and (6R)-tetrahydrofolic acid and their salts with strong bases or acids have become accessible very easily and particularly economically.

The invention also relates to the use of the (6S)- and (6R)-tetrahydrofolic acid and their addition salts according to the process of the invention for the preparation of optically pure 5,10-methylenetetrahydrofolic acids and their salts by treatment with formaldehyde. It is to be taken into consideration here that 5,10-methylene-(6R)-tetrahydrofolic acid is obtained from (6S)-tetrahydrofolic acid by reaction with formaldehyde and 5,10-methylene-(6S)-tetrahydrofolic acid is obtained analogously from (6R)-tetrahydrofolic acid.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following example, all temperatures are set forth uncorrected in degrees Celsius; and, unless otherwise indicated, all parts and percentages are by weight.

The entire disclosure of all applications, patents, and publications, cited above and below, and of corresponding Swiss Appliction 00 108/91-1, filed Jan. 16, 1991, are hereby incorporated by reference.

EXAMPLES

In the examples, the following HPLC method was employed to determine the purity of tetrahydrofolic acid, acid, 5-formyl-, 5-methyl- and 5,10-methylenetetrahydrofolic acid:

Eluant A: 0.03 M $Na_2HPO_4$ + 0.03 M $KH_2PO_4$ in water
Eluant B:
   1 part of (0.03 M $Na_2HPO_4$ + 0.03 M $KH_2PO_4$ in water)
   3 parts of methanol
   then adjusted to pH 7.8 with phosphoric acid
Gradient: from 2% eluant B to 95% eluent B in the course of 25 minutes
Column: ODS (Hypersil)
Detection: UV-300 nm The following HPLC method was employed to determine the (6S)-content:
Derivatization: Dissolve tetrahydrofolic acid or addition salt in acetonitrile/water 1:1 and react with 2,3,4,6-tetra-O-acetyl-$\beta$-D-glucopyranosyl isothiosyanate
Eluant:
   2.5 parts of acetonitrile
   1.5 parts of methanol
   6.0 parts of 0.02 M citric acid
Column: RP-8 (Lichrosphere)
Detection: UV-270 nm

EXAMPLE 1

14.3 g of toluene-4-sulfonic acid (150 mol %) are dissolved at 60° C. under nitrogen in 440 ml of water containing 0.1% of 2-mercaptoethanol. 25.0 g of pure (6R,S)-tetrahydrofolic acid are introduced in the course of 5 minutes. The resulting suspension is cooled to 40° C. The precipitated product is filtered off after 2-5 hours, washed with water and then with ethanol.

16.9 g of toluene-4-sulfonic acid addition salt of (6S)-tetrahydrofolic acid having a (6S)-content of 86.7% are obtained; determined by means of HPLC.

By recrystallization of the resulting product from a mixture of 110 ml of N,N'-dimethylformamide and 220 ml of water, toluene-4-sulfonic acid addition salt of (6S)-tetrahydrofolic acid having a (6S)-content of 97.5% are obtained; determined by means of HPLC.
$[\alpha]_D^{25} = -60.6°$ (c=0.5% in DMF)

To liberate the (6S)-tetrahydrofolic acid, 170 ml of water containing 0.1% of 2-mercaptoethanol are cooled to 10° C. under nitrogen. 5.0 g of toluene-4-sulfonic acid addition salt of (6S)-tetrahydrofolic acid are sprinkled in. 4 ml of 2 N sodium hydroxide solution are added dropwise to this suspension. After cooling to 2° C., the precipitated product is filtered off, washed with water and then with ethanol.

3.7 g of (6S)-tetrahydrofolic acid having a (6S)-content of 97.7% are obtained; determined by means of HPLC.

$[\alpha]_D^{25} = -44.5°$ (c=1% in water)

EXAMPLE 2

13 g of toluene-4-sulfonic acid (135 mol %) are dissolved at 20° C. under nitrogen in 200 ml of acetic acid and 200 ml of water containing 0.2% of 2-mercaptoethanol. 25.0 g of pure (6R,S)-tetrahydrofolic acid are rapidly introduced. The solution is seeded with a little authentic (6S)-tetrahydrofolic acid-toluene-4-sulfonic acid addition salt. After 5 hours, the precipitated product is filtered off, washed with acetic acid/water and then with ethanol.

12.7 g of toluene-4-sulfonic acid addition salt of (6S)-tetrahydrofolic acid having a (6S)-content of 93.6% are obtained; determined by means of HPLC.

10.0 of the (6S)-tetrahydrofolic acid-toluene-4-sulfonic acid addition salt thus obtained are suspended at 25° C. under nitrogen in 100 ml of water and adjusted to pH>3.5 with 30% sodium hydroxide solution. The pH of the solution thus obtained is then brought to below 1 again with 37% hydrochloric acid. After 12 hours, the precipitated product is filtered off, washed with water and then with ethanol.

8.9 g of toluene-4-sulfonic acid addition salt of (6S)-tetrahydrofolic acid having a (6S)-content of 99.7% are obtained; determined by means of HPLC.
$[\alpha]_D^{25} = -62.0°$ (c=0.5% in DMF)

EXAMPLE 3

14.30 g of toluene-4-sulfonic acid (150 mol %) are dissolved at 27° C. under nitrogen in 220 ml of L(+)-lactic acid and 220 ml of water containing 0.2% of mercaptoethanol. 25.0 of pure (6R,S)-tetrahydrofolic acid are rapidly added. The resulting solution is seeded with a little authentic (6S)-tetrahydrofolic acid-toluene-4-sulfonic acid addition salt and cooled to 20° C. After 15-20 hours, the precipitated product is filtered off, washed with lactic acid/water and then with ethanol.

15.1 g of toluene-4-sulfonic acid addition salt of (6S)-tetrahydrofolic acid having a (6S)-content of 92.5% are obtained; determined by means of HPLC.

EXAMPLE 4

14.3 g of toluene-4-sulfonic acid (150 mol %) are dissolved at 27° C. under nitrogen in 110 ml of 1-methyl-2-pyrrolidone and 110 ml of water containing 0.4% of 2-mercaptoethanol. 25.0 g of pure (6R,S)-tetrahydrofolic acid are rapidly added. The solution is diluted with 220 ml of water and cooled to 20° C. After 15-20 hours, the precipitated product is filtered off, washed with 1-methyl-2-pyrrolidone/water and then with ethanol.

13.3 g of toluene-4-sulfonic acid addition salt of (6S)-tetrahydrofolic acid having a (6S)-content of 94.7% are obtained; determined by means of HPLC.

EXAMPLE 5

1.5 g of toluene-4-sulfonic acid (150 mol %) are dissolved at 27° C. under nitrogen in 90 ml of N, N'-dimethylformamide and 90 ml of water containing 0.4% of 2-mercaptoethanol. 20 g g of pure (6R,S)-tetrahydrofolic acid are rapidly added. The solution is diluted with 180 ml of water and cooled to 20° C. After 15-20 hours, the precipitated product is filtered off, washed with N,N'-dimethylformamide/water and then with ethanol.

11.3 g of toluene-4-sulfonic acid addition salt of (6S)-tetrahydrofolic acid having a (6S)-content of 91.4% are obtained; determined by means of HPLC.

EXAMPLE 6

11.5 g of toluene-4-sulfonic acid (150 mol %) are dissolved at 27° C. under nitrogen in 100 ml of N,N'-dimethylacetamide and 80 ml of water containing 0.4% of 2-mercaptoethanol. 20 g of pure (6R,S)-tetrahydrofolic acid are rapidly added. The solution is diluted with 160 ml of water and cooled to 20° C. After 15-20 hours, the precipitated product is filtered off, washed with N, N'-dimethylacetamide/water and then with ethanol.

11.0 g of toluene-4-sulfonic acid addition salt of (6S)-tetrahydrofolic acid having a (6S)-content of 91.5% are obtained; determined by means of HPLC.

EXAMPLE 7

12 g of benzenesulfonic acid (150 mol %) are dissolved at 70° C. under nitrogen in 440 ml of water containing 0.1% of 2-mercaptoethanol. 25.0 g of pure (6R,S)-tetrahydrofolic acid are introduced in the course of 5 minutes. The resulting suspension is cooled to 60° C. After 2-5 hours, the precipitated product is filtered off, washed with water and then with ethanol.

13.8 g of benzenesulfonic acid addition salt of (6S)-tetrahydrofolic acid having a (6S)-content of 92.4% are obtained; determined by means of HPLC.

10.0 g of the (6S)-tetrahydrofolic acid-benzenesulfonic acid addition salt thus obtained are suspended at 25° C. under nitrogen in 100 ml of water and adjusted to pH>3.5 with 30% sodium hydroxide solution. The pH of the solution thus obtained is then brought below 1 again with 37% hydrochloric acid. After 12 hours, the precipitated product is filtered off, washed with water and then with ethanol.

9.0 g of benzenesulfonic acid addition salt of (6S)-tetrahydrofolic acid having a (6S)-content of 99.8% are obtained; determined by means of HPLC.
$[\alpha]_D^{25} = -63.5°$ (c=1% in DMF)

If the 150 mol % benzenesulfonic acid employed is replaced by 55 mol % benzenesulfonic acid and 50 mol % hydrochloric acid, 12.7 g of benzenesulfonic acid addition salt of (6S)-tetrahydrofolic acid having a (6S)-content of 91.6% are obtained under identical crystallization conditions; determined by means of HPLC.

To liberate the 6R-tetrahydrofolic acid, the filtrate is adjusted to pH 3.5 with sodium hydroxide solution. After cooling to 5° C., the precipitated product is filtered off, washed with water and then with ethanol.

10 g of the residue thus obtained are dissolved at 50° C. under nitrogen in 150 ml of water containing 0.1% of 2-mercaptoethanol and 30 ml of 2 N sulfuric acid. After slowly cooling to 20° C. over 15 hours and subsequently allowing to stand for 12 hours, the precipitated product is filtered off, washed with water and then with ethanol.

9.7 g of sulfuric acid addition salt of (6R)-tetrahydrofolic acid having a (6R)-content of 97.7% are obtained; determined by means of HPLC.

EXAMPLE 8

30 ml of 2M sulfuric acid are initially introduced at 60° C. with 130 ml of water containing 0.2% of 2-mercaptoethanol and 164 ml of glacial acetic acid. 20 g of pure (6R,S)-tetrahydrofolic acid are introduced in the course of 5 minutes. The resulting solution is cooled to 50° C. After 1 hour, the precipitated product is filtered off, washed with water/glacial acetic acid and then with ethanol. 11.0 g of sulfuric acid addition salt of (6S)-tetrahydrofolic acid having a (6S)-content or 65.5 % are obtained; determined by means of HPLC.

By recrystallizing 10 of sulfuric acid addition salt of (6S )- tetrahydrofolic acid trice from ( dimethylformamide/water 1:3, 3.9 g of sulfuric acid addition salt of (6S)-tetrahydrofolic acid having a (6S)-content of 94.3% are obtained; determined by means of HPLC.

EXAMPLE 9

According to in situ processes described in the literature, for example R. L. Blakley et. al. Foltes and Pterins, 1, 93–104 (1984) (6R,S)-tetrahydrofolic acid is prepared in situ and is then directly reacted further with toluene-4-sulfonic acid:

50 g of folic acid are suspended at 25° C. under nitrogen in 200 ml of water, for example according to C. Temple, J. Med. Chem., 22, 731 (1979). The pH of the solution is adjusted to 12 using about 40 g of 30% sodium hydroxide solution. After addition of 25 g of sodium borohydride (630 mol %), in 110 ml of water, the reaction mixture is heated to 70°–75° C. and kept at this temperature for 90 minutes. 30 g of toluene-4-sulfonic acid (150 mol %), dissolved in 200 ml of glacial acetic acid, are added dropwise to the solution of (6R,S)-tetrahydrofolic acid sodium salt thus obtained after cooling to 25° C. The pH of the solution is then adjusted to below 1 using 96 g of 37% hydrochloric acid. After 12 hours, the precipitated product is filtered off, washed with acetic acid/water and then with ethanol.

32.9 of toluene-4-sulfonic acid addition salt of (6S)-tetrahydrofolic acid having a purity of 82% and a (6S)-content of 95.4% are obtained; determined by means of HPLC.

3.0 g of the (6S)-tetrahydrofolic acid-toluene-4-sulfonic acid addition salt thus obtained are suspended at 25° C. under nitrogen in 30 ml of water and adjusted to pH 11.6 with about 3 g of 30% sodium hydroxide solution. 0.9 g of toluene-4-sulfonic acid (120 mol %), dissolved in 36 ml of glacial acetic acid, is added dropwise to the solution thus obtained. The pH of the solution is then adjusted to below 1 with 2.2 g of 37% hydrochloric acid. After 12 hours, the precipitated product is filtered off, washed with acetic acid/water and then with ethanol.

1.81 g of toluene-4-sulfonic acid addition salt of (6S)-tetrahydrofolic acid having a purity of 100% and a (6S)-content of 98.9% are obtained; determined by means of HPLC.

EXAMPLE 10

By the replacement of toluene-4-sulfonic acid in Example 9 by the equivalent amount of benzenesulfonic acid, the benzenesulfonic acid addition salt of (6S)-tetrahydrofolic acid can be prepared in a similar manner.

32.9 g of benzenesulfonic acid addition salt of (6S)-tetrahydrofolic acid having a purity of 80% and a (6S)-content of 94.2% are obtained; determined by means of HPLC.

EXAMPLE 11

By the replacement of toluene-b 4-sulfonic acid in Example 9 by the equivalent amount of sulfuric acid, the sulfate of (6S)-tetrahydrofolic acid can also be prepared in a similar manner.

27.1 g of (6S)-tetrahydrofolic acid sulfate having a purify of 85% and a (6S)-content of 69.2% are obtained; determined by means of HPLC.

EXAMPLES 12–18

The following can be prepared in a similar manner to that described in Examples 1–8:

12. Methanesulfonic acid addition salt of (6S)-tetrahydrofolic acid.
13. Ethanesulfonic acid addition salt of (6S)-tetrahydrofolic acid.
14. Phenylmethanesulfonic acid addition salt of (6S)-tetrahydrofolic acid.
15. Camphor-10-sulfonic acid addition salt of (6S)-tetrahydrofolic acid.
16. Naphthalene-1-sulfonic acid addition salt of (6S)-tetrahydrofolic acid.
17. Naphthalene-2-sulfonic acid addition salt of (6S)-tetrahydrofolic acid.
18. Naphthalene-1,5-disulfonic acid addition salt of (6S)-tetrahydrofolic acid.

EXAMPLE 19

50 g of sulfuric acid addition salt of (6S)-tetrahydrofolic acid obtained according to Example 8 are dissolved with 200 ml of 2 N sodium hydroxide solution at 20° C. under nitrogen in 500 ml of water. After addition of 7.5 ml of 36% formaldehyde (125 mol %), a mixture of 275 ml of glacial acetic acid and 275 ml of 2N sulfuric acid are added to the solution. After cooling to 2° C., the precipitated product is filtered off and washed through with ethanol.

39.6 g of 5,10-methylene-(6R)-tetrahydrofolic acid having a purity of 98.6% and a (6R)-content of 99.6% are obtained; determined by means of HPLC.

EXAMPLE 20

28 g of benzenesulfonic acid addition salt of (6S)-tetrahydrofolic acid obtained according to Example 10 are dissolved with 30% sodium hydroxide solution at about 25° C. under nitrogen in 130 ml of water. After the addition of 44 ml of 36% formic acid, the solution is divided and one half is treated with 3 g of NaBH$_4$. After 12 hours, it is acidified by addition of 10 ml of 37% hydrochloric acid. The precipitated product is filtered off and washed through with water and ethanol.

11 g of 5-methyl-(6S)-tetrahydrofolic acid having a purity of 95.8% and a (6S)-content of 99.5% are obtained; determined by means of HPLC.

The other half is treated with excess calcium chloride, and the product which precipitates is filtered off and washed through with water and ethanol.

14 g of 5-formyl-(6S)-tetrahydrofolic acid calcium salt having a purity of 96.2% and a (6S)-content of 99.7% are obtained; determined by means of HPLC.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process for the preparation of (6S)- and (6R)-tetrahydrofolic acid and their addition salts with sulfonic acids or with sulfuric acid, comprising the steps of reacting (6R, S)-tetrahydrofolic acid with a sulfonic acid or sulfuric acid, and fractionally crystallizing the resultant acid addition salt in the optional presence of an oxidation inhibitor to form an enriched (6S) fraction and an enriched (6R) fraction.

2. A process according to claim 1, wherein the crystallization is carried out from water or a mixture of water with either a lower aliphatic water-soluble carboxylic acid or a liquid water-soluble amide.

3. A process according to claim 1, wherein the crystallization is carried out from a mixture of water with acetic acid or lactic acid.

4. A process according to claim 1, wherein the crystallization is carried out from a mixture of water with methylpyrrolidone, formamide, dimethylformamide, or dimethylacetamide.

5. A process according to claim 1, wherein the process is conducted with a sulfonic acid selected from the group consisting of aromatic sulfonic acid having 6–14 C atoms, an araliphatic sulfonic acid having 7–9 C atoms, and an aliphatic sulfonic acid having 1–3 C atoms.

6. A process according to claim 1, conducted with benzenesulfonic acid, toluene-4-sulfonic acid, or sulfuric acid to form the corresponding addition salt.

7. A compound selected from the group consisting of:
(6S)-tetrahydrofolic acid benezenesulfonate;
(6S)-tetrahydrofolic acid toluene-4-sulfonate;
(6S)-tetrahydrofolic acid sulfate or; or
a methylsulfonic acid, ethanesulfonic acid, phenylmethanesulfonic acid, camphor-10-sulfonic acid, naphthalene-1,5-disulfonic acid addition salt of (6S)-tetrahydrofolic acid.

8. A compound according to claim 7, said compound being (6S)-tetrahydrofolic acid benezenesulfonate.

9. A compound according to claim 7, said compound being (6S)-tetrahydrofolic acid toluene-4-sulfonate.

10. A compound according to claim 7, said compound being (6S)-tetrahydrofolic acid sulfate.

11. A compound according to claim 7, said compound being a methanesulfonic acid, ethanesulfonic acid, phenylmethanesulfonic acid, camphor-10-sulfonic acid, naphthalene-1-sulfonic acid, naphthalene-2-sulfonic acid, or naphthalene-1,5-disulfonic acid addition salt of (6S)-tetrahydrofolic acid.

12. A process according to claim 1, wherein the (6S)- and/or (6R)-tetrahydrofolic acid is liberated from the resultant diastereomeric acid addition salt.

13. A process according to claim 1, wherein said reacting is conducted with benzene sulfonic acid, toluene sulfonic acid, or sulfuric acid.

14. A process according to claim 13, wherein the resultant sulfate, benzene sulfonic acid salt, or toluene sulfonic acid salt is fractionally crystallized from (1) water or (b) a mixture of water with a lower aliphatic water-soluble carboxylic acid or a liquid water-soluble amide.

* * * * *